(12) United States Patent
Mueller et al.

(10) Patent No.: US 7,202,953 B1
(45) Date of Patent: Apr. 10, 2007

(54) SCANNING MICROSCOPIC METHOD HAVING HIGH AXIAL RESOLUTION

(75) Inventors: Juergen Rolf Mueller, Hamburg (DE); Karsten Henco, Dusseldorf (DE); Rodney Turner, San Francisco, CA (US); Peter Axhausen, Destedt (DE); Rolf Guenther, Hamburg (DE)

(73) Assignee: Evotec Biosystems AG, Hamburg (DE)

( * ) Notice: Subject to any disclaimer, the term of this patent is extended or adjusted under 35 U.S.C. 154(b) by 0 days.

(21) Appl. No.: 09/868,845

(22) PCT Filed: Dec. 21, 1999

(86) PCT No.: PCT/EP99/10142

§ 371 (c)(1),
(2), (4) Date: Sep. 7, 2001

(87) PCT Pub. No.: WO00/37984

PCT Pub. Date: Jun. 29, 2000

(30) Foreign Application Priority Data

Dec. 21, 1998 (DE) ............................... 198 60 549
Dec. 21, 1998 (EP) ................................. 98124314

(51) Int. Cl.
| | |
|---|---|
| *G01N 21/55* | (2006.01) |
| *G01N 21/00* | (2006.01) |
| *G01J 3/44* | (2006.01) |
| *G01J 3/30* | (2006.01) |
| *G01J 4/00* | (2006.01) |
| *G01J 1/58* | (2006.01) |
| *G01B 11/14* | (2006.01) |
| *G02B 7/04* | (2006.01) |
| *G02B 27/40* | (2006.01) |
| *G02B 27/64* | (2006.01) |
| *F21V 9/16* | (2006.01) |
| *G01T 1/10* | (2006.01) |
| *G21H 3/02* | (2006.01) |
| *G21K 5/00* | (2006.01) |
| *H01J 65/06* | (2006.01) |
| *H01J 65/08* | (2006.01) |

(52) U.S. Cl. ...................... 356/445; 356/301; 356/337; 356/364; 356/624; 250/201.2; 250/201.3; 250/458.1; 250/459.1

(58) Field of Classification Search ................ 359/368, 359/372, 379, 384, 389; 356/237.1, 237.2, 356/237.3–237.6, 445, 300–303, 305, 319, 356/320, 326, 328, 624, 317, 337, 346, 432; 250/201.3, 578.1, 559.4, 559.04–559.08, 250/372, 458.1, 459.1, 461.1
See application file for complete search history.

(56) References Cited

U.S. PATENT DOCUMENTS

| | | | |
|---|---|---|---|
| 4,512,659 A * | 4/1985 | Galbraith et al. ......... 356/243.1 |
| 4,844,617 A | 7/1989 | Kelderman et al. | |
| 4,935,612 A * | 6/1990 | Bierleutgeb ............... 250/201.2 |
| 4,958,920 A * | 9/1990 | Jorgens et al. .............. 359/392 |
| 4,959,552 A * | 9/1990 | Saffert et al. ........... 250/559.26 |
| 5,062,715 A * | 11/1991 | Nakata et al. ............... 356/432 |
| 5,084,612 A | 1/1992 | Iwasaki et al. | |
| 5,248,876 A | 9/1993 | Kerstens et al. | |
| 5,260,578 A * | 11/1993 | Bliton et al. .............. 250/461.1 |
| 5,604,344 A * | 2/1997 | Finarov .................... 250/201.3 |
| 5,880,465 A * | 3/1999 | Boettner et al. ............ 250/234 |
| 5,932,872 A * | 8/1999 | Price ........................ 250/201.3 |
| 6,124,967 A * | 9/2000 | Toh ............................ 359/368 |
| 6,181,474 B1 * | 1/2001 | Ouderkirk et al. .......... 359/629 |
| 6,320,196 B1 * | 11/2001 | Dorsel et al. ............. 250/458.1 |
| 6,353,216 B1 * | 3/2002 | Oren et al. ............... 250/201.3 |
| 6,388,788 B1 * | 5/2002 | Harris et al. ................ 359/196 |
| 6,486,458 B1 * | 11/2002 | Schoeppe et al. ........... 250/205 |
| 6,677,565 B1 * | 1/2004 | Wahl et al. .............. 250/201.3 |

FOREIGN PATENT DOCUMENTS

| | | |
|---|---|---|
| DE | 197 13 362 A1 | 10/1998 |
| WO | 92/15034 | 9/1992 |
| WO | WO 95000871 A1 * | 1/1995 |
| WO | 95/22058 | 8/1995 |
| WO | 95/35492 | 12/1995 |
| WO | 97/48001 | 12/1997 |

| WO | 98/16814 | 4/1998 |
| WO | WO 9844375 A1 * | 10/1998 |
| WO | 98/57979 | 12/1998 |
| WO | 99/17086 | 4/1999 |

OTHER PUBLICATIONS

Japanese Publication No. 06137864, May 20, 1994.
Japanese Publication No. 09325277, Dec. 16, 1997.

* cited by examiner

*Primary Examiner*—Gregory J. Toatley, Jr.
*Assistant Examiner*—Gordon J. Stock, Jr.
(74) *Attorney, Agent, or Firm*—Birch, Stewart, Kolasch & Birch, LLP

(57) ABSTRACT

The invention relates to a method for optically detecting at least one entity which is arranged on a substrate. The at least one entity is scanned with a measuring volume using at least one radiation source and a confocal optic. During a scanning process an auxiliary focus is generated by means of at least one second radiation source and a second optic. Radiation generated by the first radiation source is collimated by a first optic and radiation generated by the second radiation source is collimated by a second optic. A retroreflection from the auxiliary focus is detected by at least one detector and is used to measuring the position of an interface and, thus, for indirectly positioning the measuring volume. The position of the auxiliary focus relative to the measuring volume is adjustable in a defined manner.

34 Claims, 7 Drawing Sheets

SCANNING MICROSCOPIC METHOD HAVING HIGH AXIAL RESOLUTION

This application is the national phase under 35 U.S.C. § 371 of PCT International Application No. PCT/EP99/10142 which has an International filing date of Dec. 20, 1999, which designated the United States of America and was published in English.

BACKGROUND OF THE INVENTION

1. Field of the Invention

The present invention relates to a method for optically detecting at least one entity on or in a substrate, preferably arranged on a support. Furthermore, fields of application of the method according to the invention as well as a device for carrying out said method are described.

2. Description of Related Art

It is known that confocal arrangements or arrangements being constructed for multi-photons-excitation due to their high axial local-resolution are suitable for reduction of background signals which are outside of the focal plane. Thus, in particular when detecting large-surface-structures, there is the problem that during the scanning process it has to be ensured that the focal plane is always situated in a desired position within the objects to be examined. Therefore it is possible that, for example, irregularities of a sample-support, the object to be examined is arranged on, lead to that the confocal measuring volume is not in the desired plane within the object but possibly detects structures adjacent said object, as for example parts of the sample-support. This adversely effects the object's registration and characterization that has to be performed. Therefore it is desired to take measures to maintain or to track the focal plane within a certain position.

"Patent Abstracts of Japan" (vol. 018, no. 436 (P-1786), Aug. 15, 1994) describes a device for detecting the focus-position suitable for automatically focussing an image-generating device or for measuring inequalities of the surface of an object to be examined. An optical fiber is used the end of which is moved along an optical axis by means of an actuator. The so produced interfering signal is used for the detection of deviation of the focus-position as well as for readjustment of the same.

"Patent Abstracts of Japan" (vol. 098, no. 004, Mar. 31, 1998) proposes a focus-detector using the principle of confocal microscopic optics. U.S. Pat. No. 5,062,715 discloses the use of a confocal autofocus system in a Michelson-interferometer designed for the measurement of surface-vibration.

U.S. Pat. No. 5,084,612 describes an image generating method for a scanning-microscope constructed in transmission-geometry. Herein, the position of an apertured diaphragm used for detection is tracked in a manner that possible deviation of transmitted light occurring in proximity of (in the section of?) the sample because of refraction-effects are compensated. However, it is not the object of said method to track the position of the measuring focus within the sample.

PCT/US95/01886 (international publication number WO 95/22058) describes a confocal detection device having an automatic focussing mechanism including a confocal apertured diaphragm. The autofocusing is realized in three steps. First, a laser is focused on the back side of a substrate having the sample applied thereon. In a further step the focus is positioned in a plane above the substrate. It is only in a third step, that after passing the desired position on the surface of said substrate the exact position of the surface is determined and the focus is adjusted on the substrate-surface. This process is performed at the four corners of the substrate which is an extremely time-consuming procedure. It is not possible to operate the autofocussing system during the actual measurement of the sample and the focus-height is estimated by interpolation. Hereby, not acceptable positioning defaults may occur, in particular with substrates which are not plan, as they are normally used in laboratories for cost reasons.

SUMMARY OF THE INVENTION

Therefore, it is the object of the present invention to provide a method which allows a reliable detection of sheet-like or three-dimensional structures, preferably being arranged on a sheet-support, in a detection device with high axial resolution, in particular a confocal microscope. Further, a device for carrying out the method shall be provided.

The invention provides a method or a device for optically detecting at least one entity on and/or in a substrate, preferably being arranged on a support, whereby a representative portion of the substrate having the entity applied thereto is scanned with a measuring volume by means of at least one device being confocal or configured for multi-photon-excitation, thereby receiving measuring values of optical parameters. These measuring values are then handled by means of signal processing for characterization of the at least one entity. During the time period of the recording of the measuring values the at least one entity substantially remains in its position in respect to the substrate and/or the support. The substrate has a refraction-index which is different from the one of the at least one component adjacent to the substrate. For example, the adjacent component may be a support having the substrate applied thereon. However, the substrate may also directly abut to an immersion-fluid, to air or to a component covering the substrate, as for example a covering glass.

According to the invention an auxiliary focus is generated before and/or during the scanning process, the auxiliary focus being positioned at least partly on the interface between the substrate and the adjacent component or another suitable interface. This interface has a defined spatial relation to the entity. Thus, for example, the entity (for example macromolecules as proteins or nucleic acid to be examined) could be embedded in a substrate (for example a gel) which is positioned on a support (for example a sample-support made of optical glass). It is the function of the auxiliary focus to determine the position of the interface and, in particular, to enable the detection of the distance between the interface and the optic generating the auxiliary focus. According to the invention auxiliary focus and measuring volume have a defined position to each other that is adjustable by the user. Thus, it is possible to also track the position of the measuring volume relative to the interface by tracking the position of the auxiliary focus. Thus, the distance of the measuring volume from the interface can be selected by the user.

By means of a confocally arranged detector the intensity of the light retroreflected by the interface is detected. Said intensity has a maximum value in case the auxiliary focus is positioned in direction of the optical axis of the interface. The intensity of the retroreflection decreases when the auxiliary focus is moved on the optical axis in the direction towards the substrate or the component adjacent to the substrate. Alternatively, a plurality of detectors may be positioned along the optical axis of the optic generating the auxiliary focus, in front of and/or behind the image-plane, and the ratio of the detected intensities can be determined.

Thus, the invention is characterized in that the tracking preferably may be performed online during the entire measuring procedure and thereby, the measuring volume may always be guided in a defined plane with selectable distance from the interface. The sensitivity of the focussing device to deviations from the set-position is preferably higher than the corresponding sensitivity of the confocal measuring device as it is described as follows.

In a preferred embodiment the auxiliary focus is generated by means of the same optic also serving for generation of the measuring volume. It is even possible to use the same radiation source for the generation of auxiliary- and measuring focus. Such a radiation source emits, for example, light of different wavelengths or polarization which is separated by suitable optical components and, thus, can be supplied to the respected ray paths.

To enable the desired positioning of the auxiliary focus and, thus, also indirectly of the measuring volume, before and/or during the scanning process it is desirable to find out whether the position of the auxiliary focus from the interface deviates in the direction towards the substrate or in the direction towards the component adjacent to the substrate. According to the invention the following solutions are proposed.

In a first preferred embodiment the position of an auxiliary focus relative to the interface is varied substantively along the optical axis and the intensity of the retroreflection is registered depending on the movement (see FIGS. 1, 2, 3, 5 and 6). Hereby, for example, the focussing optic is movable upward and downward along the optical axis. However, it is also possible to move the substrate which is, for example, arranged on a support positionable directly or indirectly in z-direction. Furthermore, it is possible to vary the divergence of the ray-bundles serving for generation of the auxiliary focus. Preferably, the movement is performed periodically. The intensity detected by the confocal arranged detector will be raised each time when the distance between reflected interface and auxiliary focus is reduced. In turn, the intensity will be reduced when said distance is raised by the movement. Thus, it is detectable by the direction of movement leading to a raise or reduction of the detected intensity in which direction the position of the auxiliary focus deviates from the position of the interface and the deviation can be corrected, respectively.

Preferably, the amplitude of the movement has to be selected so that a simultaneous recording of measuring values from the measuring volume will not be disturbed. Thus, the amplitude of movement will normally correspond to the axial extent of the measuring volume or will be smaller than said extent. In the latter case, the extension of the confocal detected volume of the auxiliary focus—in particular in the direction of the respective optical axes of the objectives used for generation of auxiliary focus and measuring volume—should be smaller than the extent of the measuring volume. Such a small extent may preferably be provided in a manner such that the auxiliary focus is generated by means of an optic having a numeric aperture which is larger than the numeric aperture of the optic used for generation of the measuring volume. Alternatively, also merely a smaller part of the numeric aperture of a common optic or of the respective optics may be utilized for generation of the measuring volume than for the generation of the auxiliary focus. In a further variation a confocal arranged diaphragm is used at the detection of the auxiliary focus, whereby the diaphragm comprises a smaller opening than a confocal arranged diaphragm used for the detection of the measuring volume.

In a second preferred embodiment, the position of the auxiliary focus relative to the interface is moved both, laterally to the optical axis of the optic generating the auxiliary focus and axially. The analysis of the retroreflection may be performed in a manner corresponding to that of the embodiment described before.

In the third preferred embodiment, the intensity of the retroreflection is detected by means of at least two detectors arranged along the optical axis. Therefore, the light of the auxiliary focus reflected from the interface is, for example, divided up on the detectors by means of semi-reflecting mirrors. Preferably, the detectors are arranged in different distances from the focusing optic, in particular in front of and behind the focal plane, so that—depending on the position of the auxiliary focus relative to the reflecting interface—different portions of the reflected intensity are detected by the detectors. Thus, it can be determined from the distribution of the intensity detected by the detectors in which direction the position of the auxiliary focus deviates from the position of the interface. This is exemplary shown in FIG. 4.

For example, two detectors arranged at the same distance from the focal plane in front of and behind said plane, respectively, detect an intensity-ration of 1:1, if the auxiliary focus is placed on the interface. According to the direction of deviation of the auxiliary focus from the interface the intensity detected by one of the detectors increases.

A so determined deviation of the auxiliary focus from the desired position is correctable in all embodiments by a corresponding tracking, which, if necessary, is superimposed the above described movement. Preferably, the auxiliary focus is tracked in a manner that it is positioned on the interface.

To make the apparative efforts as little as possible it is desired to generate the auxiliary focus with the same optic that also serves for generation of the measuring volume. In such an embodiment of the invention semi-reflecting mirrors, for example, may be utilized to concentrate the rays generating measuring volume or auxiliary focus, respectively, in front of the objective as well as to separate the detected radiation reflected from the measuring volume or auxiliary focus, respectively. If it is desired, for example, to arrange measuring volume and auxiliary focus in adjustable distance from each other substantially along the optical axis, it is useful to connect suitable optical elements (e.g. lenses, convex and concave mirrors) in front of the objective on the side opposite to the sample to generate two bundles of rays of different divergence or convergence, respectively, which are then focused from the objective to the measuring volume and to the auxiliary focus, respectively.

On the other hand an arrangement can be selected, wherein measuring volume and auxiliary focus are generated by means of separate optics. In this case, both of the optics are advantageously connected mechanically or are controllable in a manner such that a tracking of the auxiliary focus affects a respective tracking of the measuring volume. Also in this embodiment measuring volume and auxiliary focus may either fully or partly overlap, or they may be arranged spacially separate from each other. The positioning of auxiliary focus and measuring volume to each other may in this case be adjusted by means of adjusting the positions of said two objectives to each other.

It might be preferred to generate the excitation ray path both, for the measuring volume and for the auxiliary focus, by means of one single radiation source optionally capable of emitting radiation of different wave lengths. On the other hand, in particular in the case of spacial separation of measuring volume and auxiliary focus, it might be preferred to use two separate radiation sources. The radiation sources can be, for example, a laser, a light-emitting diode, filament- or electric discharge lamps. Suitable detectors known by a person skilled in the art are, for example, photodiodes of the Avalache-type or other photodiodes as well as a photomultiplier. Means for single-photon-detection are preferred.

In a further embodiment of a method and apparatus according to the invention it is in particular advantageous to select an objective having a high numeric aperture, preferably higher than 0.9, and/or a small operating-distance for generating the measuring volume and/or the auxiliary focus. The selection of a smaller operating-distance, in particular smaller than or equal to one millimeter, is in particular favorable measuring the fluorescence in the measuring volume. Absorption of the fluorescence-light taking place in the emission-trace of the rays reduces the counter rate per molecule, i.e., the fluorescence-intensity detected per molecule. In contrast to the expectation this effect apparently linearly or more than linearly affects the signal-noise-ratio, so that a small operating distance is of advantage.

Preferably, the scanning process may be performed as follows. A confocal microscope is used for optically detecting volume to be observed having a radiation source, preferably for generating an excitation-light, a dichroic mirror from which entering radiation of the radiation source is reflected, an arrangement of objective lenses comprising a mechanical aperture, whereby said arrangement receives the radiation reflected by the dichroic mirror and focuses said radiation on the volume to be observed, and an observing-optic-arrangement receiving the radiation coming from the volume to be observed and passing through the dichroic mirror. Between the dichroic mirror and the objective-lense-arrangement a reflection-mirror-arrangement is positioned preferably having a plan deflection-mirror on the objective side which is arranged oscillable around a standard-point-position. When the mirror on the objective side is oscillating the optical axes of the respective reflected excitation-light cross each other in a substantially common intersecting point in the portion of the mechanical aperture of the objective-lens-arrangement. The oscillation axis of the mirror on the objective side corresponds to the intersecting line of the plane that is fixed by the deflection-mirror on the objective side with the plane extending through the common intersecting point of the optical axes of the reflected radiation and perpendicular to the optical axis of the reflected radiation, when the deviation mirror on the objective side is situated in its standard-point-position. A corresponding device is known from PCT/EP97/03022 (international publication number WO 97/48001) the disclosure of which is incorporated herewith by reference. But also other methods known by persons skilled in the art may be used for deviation of the ray which is generated by the radiation source. Optionally, it is also possible to vary directly or indirectly the position of the substrate or of the used microscope-optic(s).

For example, diffused light intensities, fluorescence intensities at least one wave-length, fluorescence intensities in dependence on the polarization, fluorescence durabilities and/or molecule luminosities are detectable as optical parameters. Thereby, it might be preferred, to determine molecule luminosities according to the method described in WO-A-98/16814. Therein it is described that intensity fluctuations of emitted radiation from particles being placed in a measuring volume are observed by means of a detector, whereby said method comprises the following steps: repeated measurement of the number of the photons per time-interval defined length; determination of a function, as for example a distribution function, of the number of photons per time-interval; and then determination of the function, as for example again a distribution function, of the specific particular luminosities based on the function of the number of photons per time interval. Also reference is made how the function of the number of photons can be processed or how, for example, instrumental parameters can be taken into consideration in an adequate manner. Physical properties of particles, especially particular luminosities, may also be determined as it is disclosed in PCT/EP98/06165. The method described therein comprises the following steps: repeated measurement of the duration of time segments between detected photons; determination of a function, e.g., a distribution function of the duration of said time segments; and then determination of a function of specific physical properties of the particles to be examined based on said function of duration of the time segments. In particular, in relation to experimentally determined and theoretic function of the duration of the time segments a fitting process is proposed, whereby, with regard to the theoretic function, parameters of a spacial luminosity-function that is characteristic for the instrumental arrangement are taken into consideration. It is proposed to examine, e.g., fluorescence-polarization, fluorescence-intensities depending on wave length, fluorescence-durability, energy transfer etc. In a further embodiment it might be of advantage to determine a plurality of optical parameters to obtain an improved characterization of the entity. In particular, this can be performed by means of the method described in PCT/EP98/03505. The following method is proposed therein: determination of intensity-fluctuations of emitted radiation from particles situated in a measuring volume by means of at least one detector; determination of intermediate statistical data comprising an at least two-dimensional statistic function based on said intensity-fluctuations; determination of information based on the intermediate statistical data. In the last step, for example, the mutual occurrence of two properties at one particle can be examined. Reference is made to the disclosure of the mentioned published patent application, in particular in relation to the physical properties to be examined of the examining particles, their determination as well as the determination of the intermediate statistical data, the disclosure is incorporated herewith by reference.

The method according to the invention and the apparatus used to perform said method are suitable, for example, for detecting optical parameters of entities as molecules, molecule complexes, polymers, vesicular structures, of, e.g., built up particles of polymers or inorganic materials, cells, bacteria and virus. They can, for example, be arranged on mineral or organic substrates. In particular, said substrates may consist of polymeric gels, particles built up from polymeric or inorganic materials, vesicular structures, cells, bacteria and virus.

In a further embodiment, a-priori-information of the distribution and/or structure of the entities and/or of the substrates are used in the signal processing. So it is possible, for example, to use bacteria or polymeric balls (so called beads) as a substrate, on the surface or in the interior of which in particular entities of the same kind are arranged, respectively. In signal processing, it is often helpful, to take into consideration a-priori-information concerning the substrate to be examined, as for example the structure, the spacial extent, the arrangement, etc. of said substrate to be capable, by means of signal processing, in particular image processing, of identifying measuring values as belonging together. Further, it might be of advantage, to form mean values over the measuring values belonging to entities identified as equivalent or to evaluate said measuring values statistically in a different manner to form the characterization of the entities more significant. Methods of object-identification known in literature as, for example, Hough-Transformation, Template Matching and correlative methods can be used as methods for signal processing. Said methods are described in literature (see, for example, E. R. Davies, Machine Vision: Theory, Algorithms, Practicalities; Academic Press, London—San Diego, $2^{nd}$ edition, 1997).

It is often desirable, to separate excellent entities and/or substrates from the other entities and/or substrates by means of certain optical parameters to subject them to a further analysis and/or processing. This separation can be performed by means of a suitable manipulator, as for example a pipette, a mechanical gripper etc. Especially suitable methods are, for example, described in U.S. 2002/0073787 A1 published Jun. 20, 2002, the disclosure of which is incorporated herewith by reference. For example, the removal or separation, respectively, by means of electric potential- or field impulse, of pressure-difference-pulse or also of light-pressure-pulse is described therein. It is also possible to use a preferably piezo-controlled pump- or dispension-system, respectively. In general it is helpful to detect the determined measuring values depending on the position of the measuring volume during the scanning process for automation of the separation process.

In particular, the method and the corresponding device can be used in research of active ingredients, functional analysis of combinatoric-chemical of combinatoric-biological synthesis-products, functional genom-analysis, evolutive biotechnology, diagnostics material examination or proteom-analysis, or the investigation of material.

In one embodiment of the method according to the invention, for example, bead-structures are used as substrate, said bead-structures are occupied by a plurality of entities of the same kind or comprise said entities. For example, said entities may be a result of a process of the combinatorial chemistry, whereby normally the actual structure of the entity is unknown. Preferably, the entities comprise detectable markers, as for example fluorescence-colors. This variation has the advantage that it is not necessary that the reacting agents added later comprise detectable markers. Preferably, the substrates are arranged on a support, as for example microfilter-plates with a plurality of recesses or a sheet-like structure. In this embodiment the upper- or lower surface of the support may be used as a interface for tracking the auxiliary focus and the measuring volume. Reacting agents are added, the interaction of which with the entities are to be examined. In an embodiment, these reacting agents may also comprise detectable markers. Thereafter, the substrate is scanned, for example, to find potential binders of the reacting agents among the entities and/or to produce a chemical reaction. The bond between the reaction agent and the entity may be characterized by means of the optical parameters described above in more detail. Complexes having desired properties between reacting agent and entity may be separated from the other entities or substrates, respectively, to subject them to further analysis and/or treatment. Preferably, the described method is applicated in the search for active ingredients.

In a further variation a cleavable linking structure is arranged between the substrate and the entities having a detectable marker applied thereto. Thus, for example, in a process of chemical syntheses cleavable linking structures may be arranged on substrates, as polymeric beads, said linking structures are connected with fluorescence-colors to which the entities to be examined are synthesized thereafter, preferably in a combinatoric method. This variation has the advantage that after selection of beads carrying complexes with desired properties between the reacting agents and the entity a separation of the color-marked entity may happen, said entity can be analyzed thereafter in a so-called dissolving assay. This variation is also in particular suitable for the searching of active ingredients.

In a further embodiment substrates with entities of known structure are used whereby all substrates comprise the same entities. Preferably, the substrates are also distributes on recesses of microtiter or nanotiter plates herein. Thereafter, a solution of reacting agents known to be interactive with the entities are added to the recesses. Further, solutions of active ingredients of different potential are added to the recesses to find out if said active ingredients are suitable to influence the interactivity between entity and reaction agent.

The above-described embodiments may also be performed with biological substrates as for example virus, phages, bacteria, fungals or eucaryotic cells. Thus, for example, natural or cloned entities can be examined preferably on the surface of said biological substrate with the advantage that here is a coupling between the as desirable identified phenotype with its corresponding genotype. Such a proceeding is known under the pertinent term of phage-display or cellular-display.

In a further application the method according to the invention may also be helpful in cellular reporting assays. The precision of the scanning method, in particular the exact local resolution, allows the observation of the exposure and/or intracellular translocation of substances having a surprising high local resolution as well as quantification-precision.

The method according to the invention allows also in an advantageous manner the examination of paths of signal-transduction. In particular it is also characterized in that it is possible to work with primary cells and thus, an upregulated expression of the entities to be examined, as for example receptors, can be renounced.

Furthermore, the method is applicable in the so-called differential display, wherein cells of effected persons can be compared with those of healthy persons. Further possibilities of comparison comprise: treated/untreated cells, wild-type/mutants, etc.

Further applications relate to examinations of molecular interactions, as for example protein-protein-interactivities and protein-nucleic-acid-interactivities. In particular, it is also possible to examine interactivities between proteins and peptides of unknown nature or function with ligandes of potential physiological significance, however, the structure of which is often not cleared up yet. Hereby, preferably at least one agent will be coupled chemically or adsorbedly with a particular structure.

It can also be preferred to apply the method according to the invention as well as the corresponding device in the field of gelelectrophoreses. In combination with the separation or isolation step, respectively, certain entities on the gel serving as a substrate can be directly directed to another analysis or also duplication (PCR, etc.).

The method and the device according to the invention are also applicable for detection and preferably for isolation of cell types rare to be found, as this is the case, for example, in the prenatal-diagnostics, in the oncology or in general in the pathology.

BRIEF DESCRIPTION OF THE DRAWINGS

Preferred embodiments according to the invention are described in the following.

DETAILED DESCRIPTION OF THE INVENTION

Figure 1:
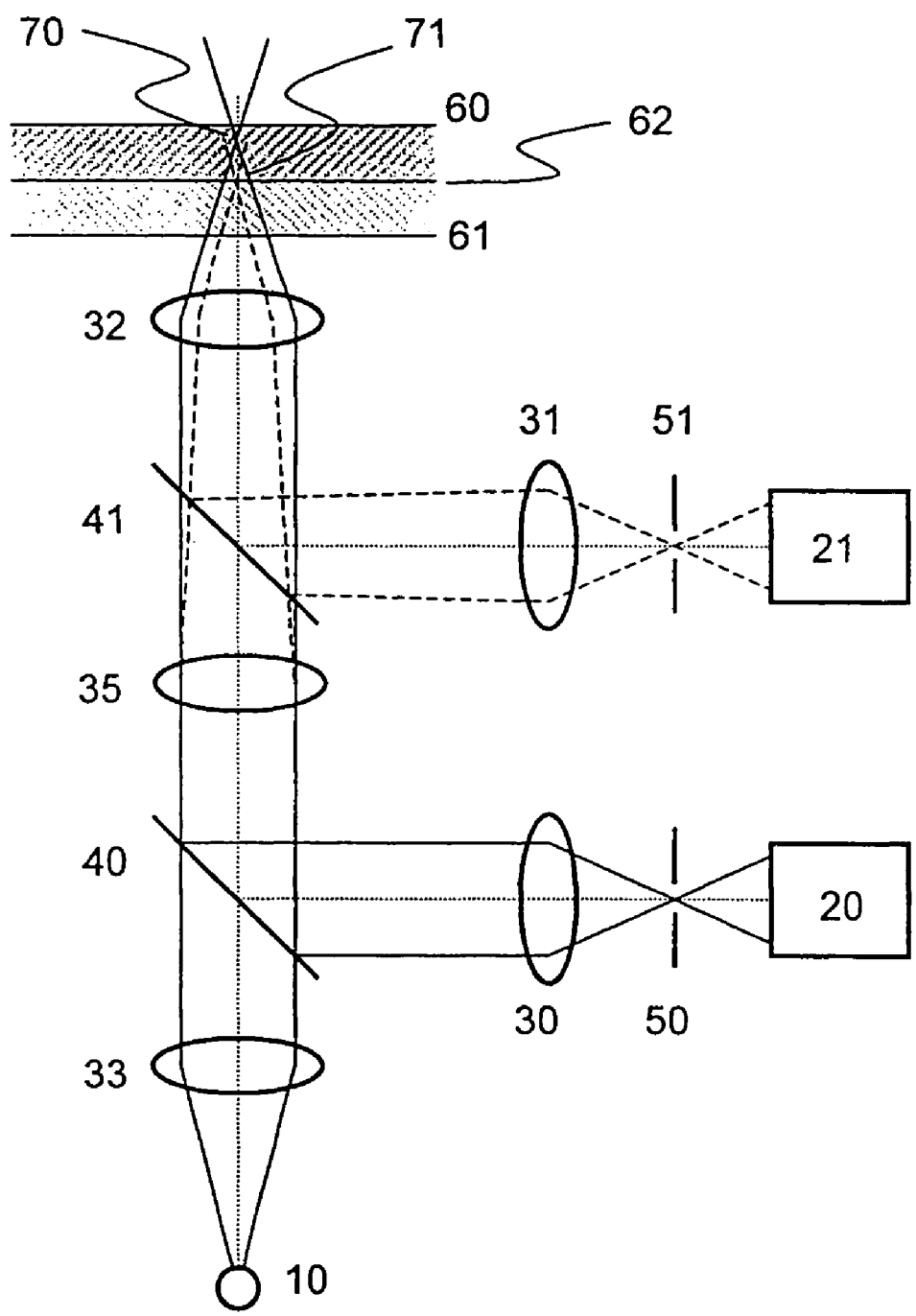
FIG. 1 is a schematical view illustrating a confocal microscope arrangement having a radiation source and two detectors one of which detecting signals from the auxiliary focus and the other signals from the measuring volume.

First of all, FIG. 1 shows a confocal arrangement: The radiation from a radiation source 10 is collimated by an optic 33 and focused by an objective 32 on a substrate 60 to be examined. The radiation source 10 emits light of different wave lengths. Exchangeable optical means 35 having a refractive power dependent on the wave length separate said light in bundles of different convergence, said bundles are focused in different positions by the objective 32 thereby generating an auxiliary focus 71 and a measuring volume 70. Thus, the desired distance between auxiliary focus 71 and measuring volume 70 is adjustable by the user by selecting the lens 35. In the illustrated exemplary arrangement the auxiliary focus 71 is situated on the interface 62 between substrate 60 and support 61, whereas measuring volume 70 is situated in the substrate 60. Scattered or fluorescent radiation emerging from the measuring volume 70 is bundled once again by the objective 32 and is fully or semi reflected by the beam splitter 40 being constructed, for example, as a mirror that is fully or semi reflecting. By an optic 30, the reflected radiation is focused on a diaphragm 50 arranged confocal with a measuring volume 70. The radiation passing through the diaphragm falls onto the detector 20 serving for receiving the measuring signals. The diaphragm 50 is not required when using multi-photonen excitation.

By means of a further beam splitter 41, an optic 31 and a diaphragm 51 also arranged confocal, a part of the radiation from the auxiliary focus 71 reflected at the interface 62 is directed to the detector 21. In the arrangement according to present Figure the focusing optic 32, for example, is moved upward and downward along the optical axis to be able to determine the current position of the auxiliary focus 71 relative to the interface 62 and to readjust, if need be. Thus, an indirect follow up of the measuring 70 is ensured.

Figure 2:
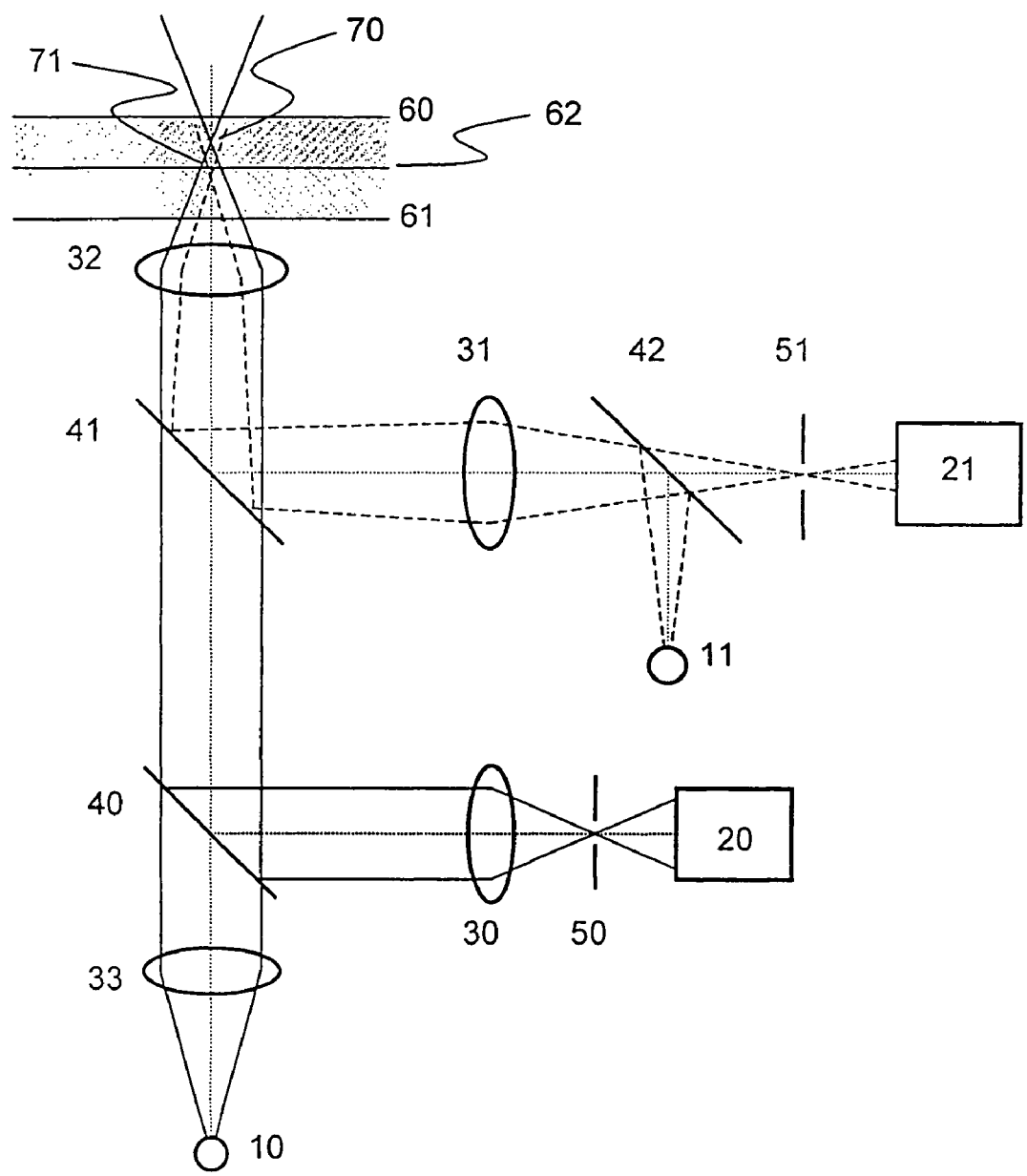
FIG. 2 is a schematical view illustrating another embodiment of a confocal microscope arrangement according to the invention, wherein measuring volume and auxiliary focus are arranged along the optical axis separately from each other. The arrangement includes an additional radiation source for generating the auxiliary focus.

FIG. 2 shows another variation of the confocal arrangement, wherein the measuring volume 70 and the auxiliary focus 71 are arranged along the optical axis separately from each other. The conventional confocal radiation- and detection unit consisting of radiation source 10, detector 20 and the corresponding optical elements has already been described in FIG. 1. In this embodiment a separate radiation source 11 is used for generation of an auxiliary focus 71. In the shown example, the light of said radiation source reflected from beam splitter 42 is bundled to a converging beam by the optic 31, so that the auxiliary focus 71 generated by the objective 32 is positioned closer to the objective 32 than the measuring volume 70 resulting from focusing a parallel bundle of rays by means of the objective 32. The auxiliary focus 71 again is arranged on the interface 62 between the substrate 60 and the support 61; the radiation reflected at the interface 62 is focused on the confocal arranged diaphragm 51 by means of the objective 32 and the optic 31 and detected by the detector 21. In this embodiment the auxiliary focus 71 can be arranged in a selectable distance from the measuring volume 70 by suitable positioning the optic 31. Preferably, the auxiliary focus 71 is positioned on the interface 62 and the measuring volume 70 is generated in a desired distance from an auxiliary focus 71 within the substrate 60. In a further embodiment the auxiliary focus 71 can be generated by a bundle of rays being divergent in front of the objective 32, thus, the auxiliary focus 71 is arranged in a greater distance from the objective 32 than the measuring volume 70. Advantageously, the searching-and adjusting mechanism described in FIG. 1 can also be used in this embodiment.

Figure 3:
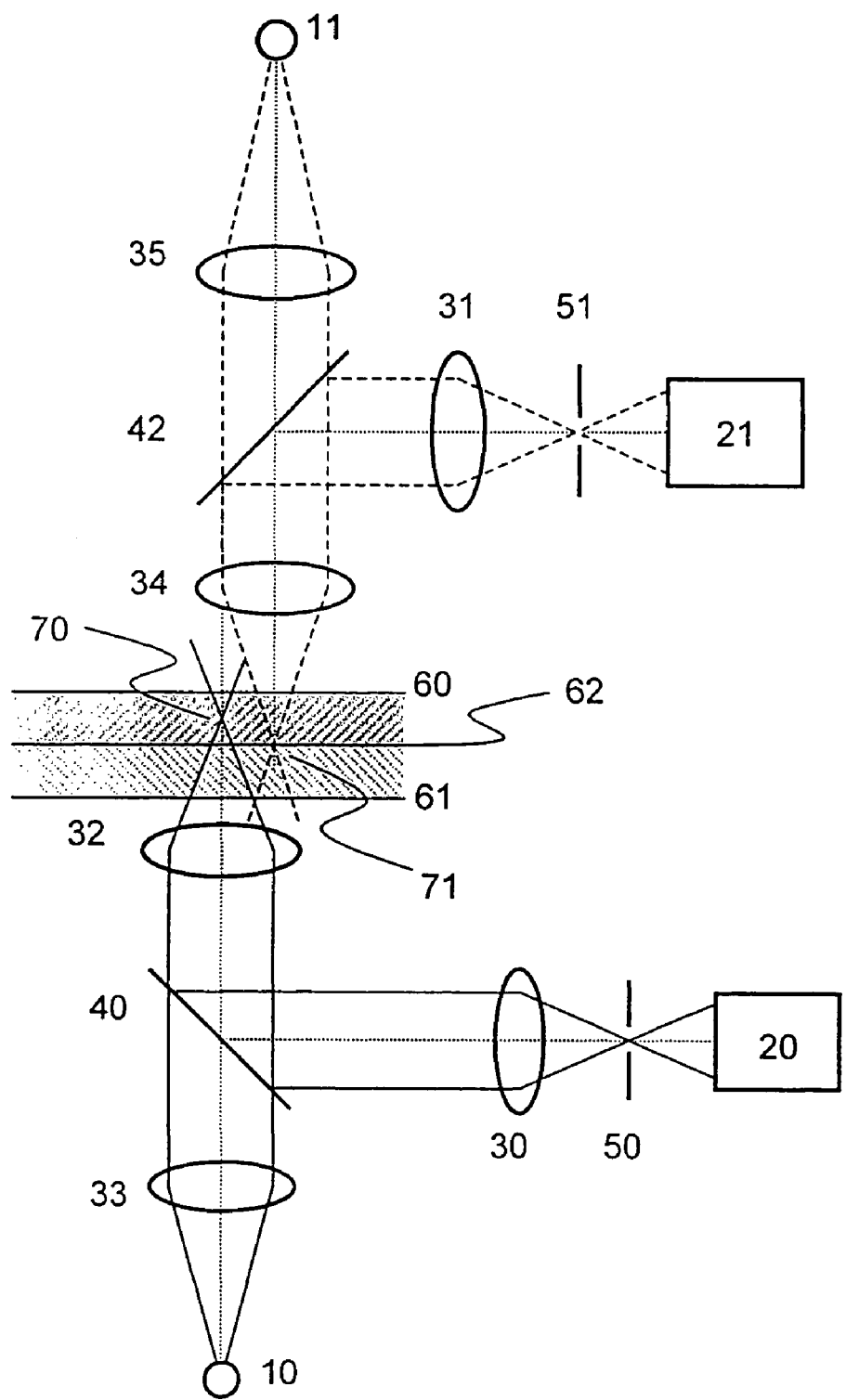
FIG. 3 is a variation, wherein separate optics are used for generation of auxiliary focus and measuring volume. As it is exemplary shown auxiliary focus and measuring volume are positionable separately from each other both in axial and lateral direction.

FIG. 3 shows a further embodiment according to the invention, wherein a separate objective 34 is applied for generation of the auxiliary focus 71. The measuring volume 70 is once again generated and imaged by the objective 32; the components of the conventional confocal arrangement arranged behind the objective 32 are already discussed in FIG. 1. The positions of the objectives 32 and 34 are controllably or mechanically connected with each other. For generation of the auxiliary focus 71 a separate radiation source 11 is used, the radiation of which is collimated by an optic 35 and focused on the interface 62 between substrate 60 and support 61 by the objective 34. Radiation reflected from the auxiliary focus 71 is once again bundled by the objective 34 and reflected by the ray-divider 42. The reflected radiation is focused by an optic 31 on a diaphragm 51 confocal with the auxiliary focus 71; the radiation passing through the diaphragm 51 hits the detector 21. In the exemplary illustrated arrangement the auxiliary focus 71 and the measuring volume 70 are arranged separately from each other in axial as well as lateral direction. Advantageously, the searching- and adjusting mechanism described in FIG. 1 can also be used in this embodiment.

Figure 4:
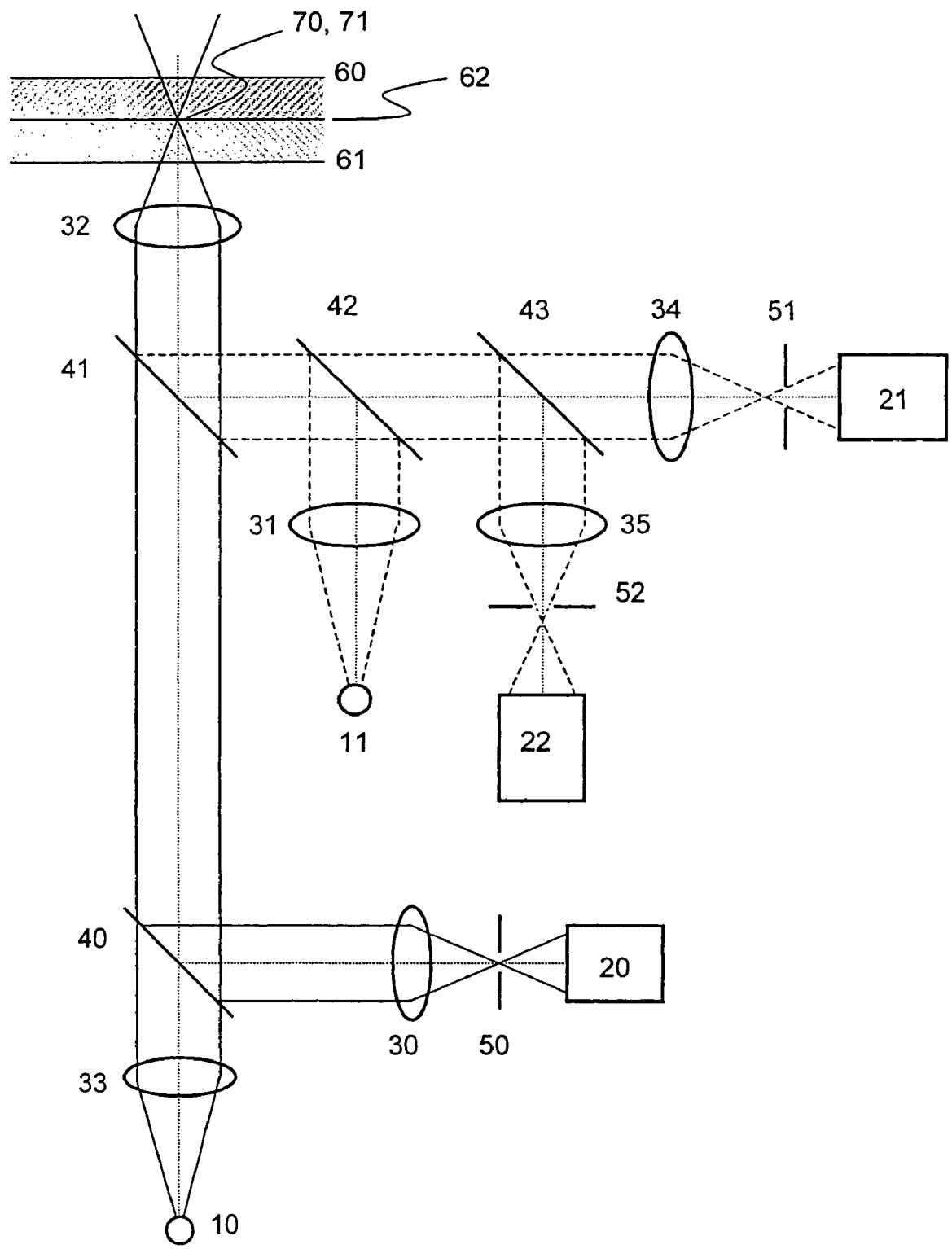
FIG. 4 illustrates a further embodiment of the invention, wherein the auxiliary focus and measuring volume are anew generated by the same optic. In this variation two detectors being displaced from each other along the optical axes to detect the direction of deviation of the position of the auxiliary focus are used for the light that is reflected by the auxiliary focus.

FIG. 4 shows a variation of the embodiment according to the invention shown in FIG. 2, wherein two detectors 21, 22 are applied for the light reflected by the auxiliary focus 71. Arrangements of two or more detectors can also be used for the embodiments according to FIG. 1 or 3, respectively. The conventional arrangement for exposure to rays and observation of the measuring volumes 70 is executed as discussed in FIG. 1. In the shown arrangement measuring volume 70 and auxiliary focus 71 are adjusted congruent. However, it is possible, to adjust other desired distances between measuring volume 70 and auxiliary focus 71 by positioning lenses 30 to 35 in a different manner.

The auxiliary focus 71 is once again located on the interface 62 between substrate 60 and support 61. The radiation reflected at the interface 62 is directed through the objective 32 and the radiation-divider 41 in direction to detectors 21,22. The radiation is divided on the detectors 21,22 by further ray-dividers 43. Both detectors are arranged in front of focusing optics 34,35 as well as diaphragms 51,52. The diaphragms 51,52 are thereby arranged in front or behind the confocal position, respectively, when the auxiliary focus 71 is placed on the interface 62. If now the relative position of auxiliary focus 71 and interface 62 to each other is changed, the detectors 21,22 will detect a changed intensity distribution of the retroreflexes. Dependent on the direction of the variation of position of the auxiliary focus 71 being displaceable in direction of the substrate 60 or the support 61 either a higher or a lower intensity of radiation originated from the auxiliary focus 71 will hit on the detector 21 or the detector 22. Thus, the searching movement described in FIG. 1 is not required.

Figure 5:
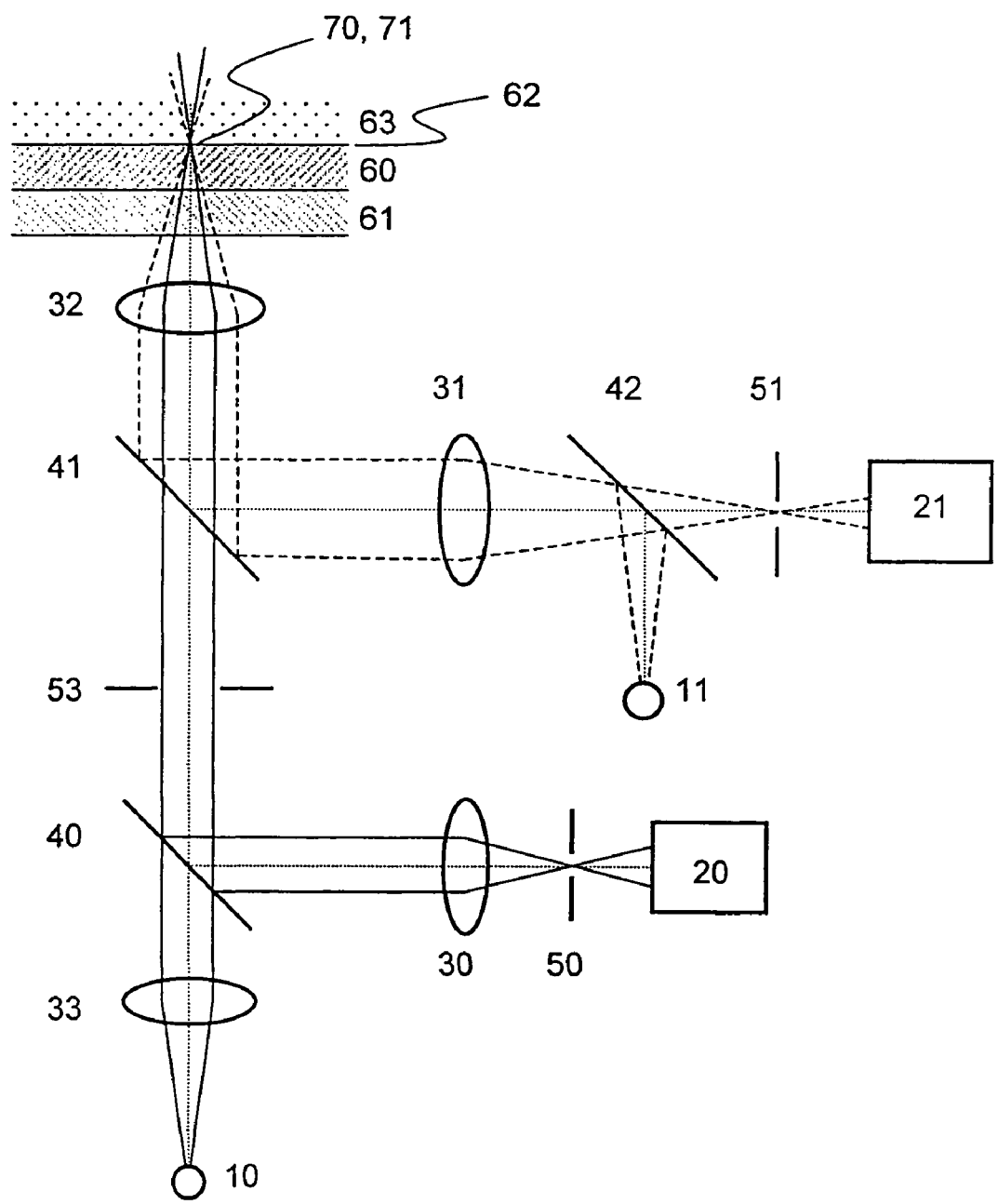
FIG. 5 shows an embodiment of the present invention, wherein the transition from a substrate to an adjacent air layer serves as a interface. Different sizes of auxiliary focus and measuring volume are obtained by different utilization of the numeric aperture of the used objective.

FIG. 5 shows a further variation of the embodiment according to the invention illustrated in FIG. 2. The conventional arrangement for radiation and observation of the measuring volumes 70 has already been discussed. In the exemplary shown arrangement measuring volume 70 and auxiliary focus 71 are adjusted congruent; however, their relative position to each other can be changed by suitable positioning of lens 31. Now, the transition between substrate 60 and adjacent air 63 serves as interface 62. The optic 32 for generation of the measuring volumes 70 is only used partly concerning its numeric aperture. On the other hand there is a wide illumination on the optic 32 for generating the auxiliary focus 71. Likewise, imaging the measuring volume 70 on the confocal arranged diaphragm 50 and its corresponding detector 20 the numerical aperture of the detecting trace of the rays is limited by the diaphragm 53. This embodiment results in a smaller focus size of auxiliary focus 71 compared with the measuring volume 70. Thus, the amplitude of the searching movements of the auxiliary focus 71 described above can be selected so small that the receiving of measured values from the measuring volume 70 almost remains uninfluenced and, nevertheless, any deviations of the auxiliary focus 71 from the interface 62 can be detected and corrected.

Figure 6:
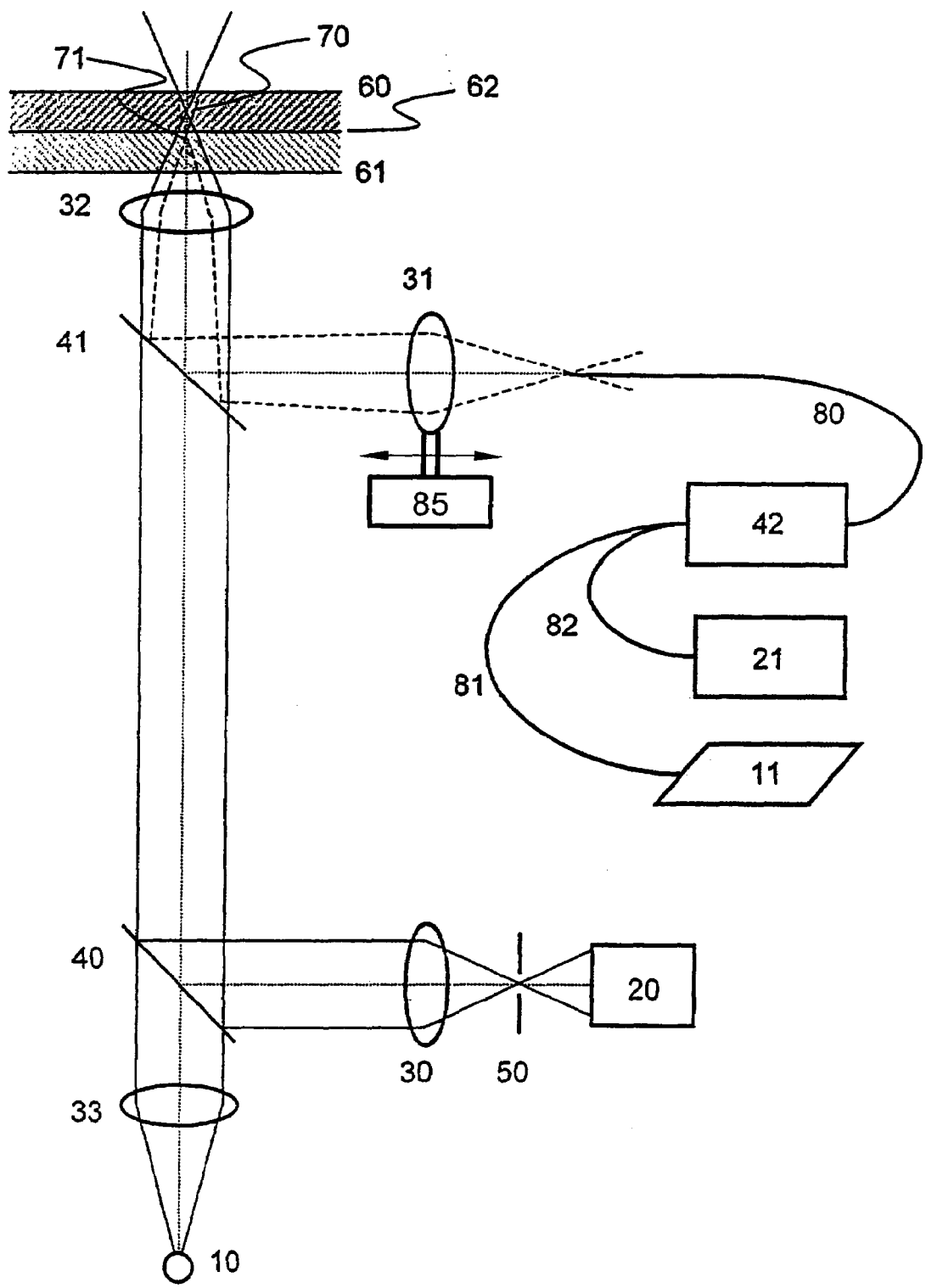
FIG. 6 shows an embodiment with a fiber optic coupling.

FIG. 6 shows a further embodiment of the optical arrangement for performing the inventive method according to FIG. 2. The conventional arrangement for radiation and observation of the measuring volume 70 has already been discussed above. Preferably, a semiconductor laser, the output radiation of which is coupled in an optical fiber 81, is used for generation of the auxiliary focus 71. The optical fiber coupling 42 corresponds to the conventional ray-divider in FIG. 2. In this embodiment the radiation of the auxiliary focus 71 is coupled in the core of an optical fiber 80 replacing the function of the apertured diaphragm 51 illustrated in FIG. 2. After passing the optical fiber coupling 42 the radiation is directed on a detector 21 by an optical fiber 82. The optical fibers can be of single or multi mode types.

Figure 7A:
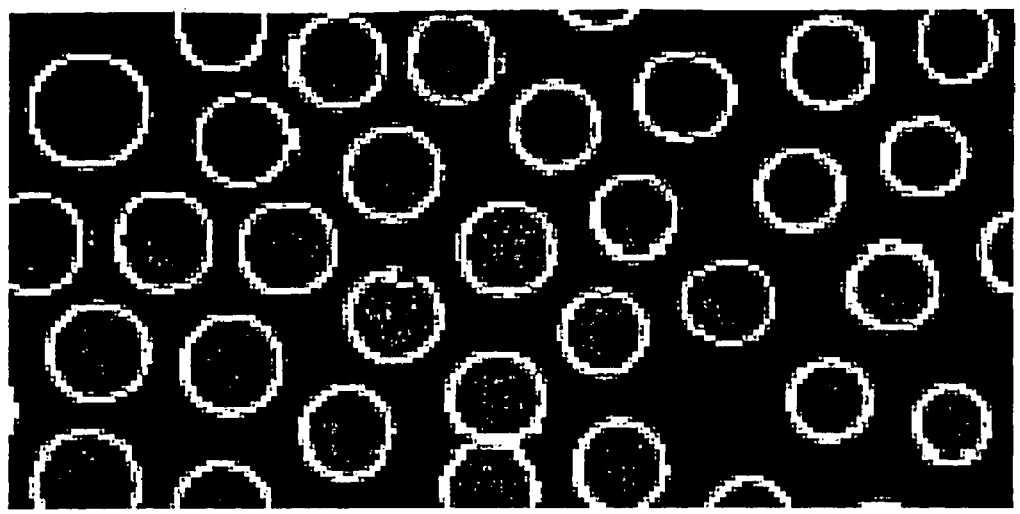
FIGS. 7 *a* and *b* show the result of the experiences illustrated in example 2.
Figure 7B:
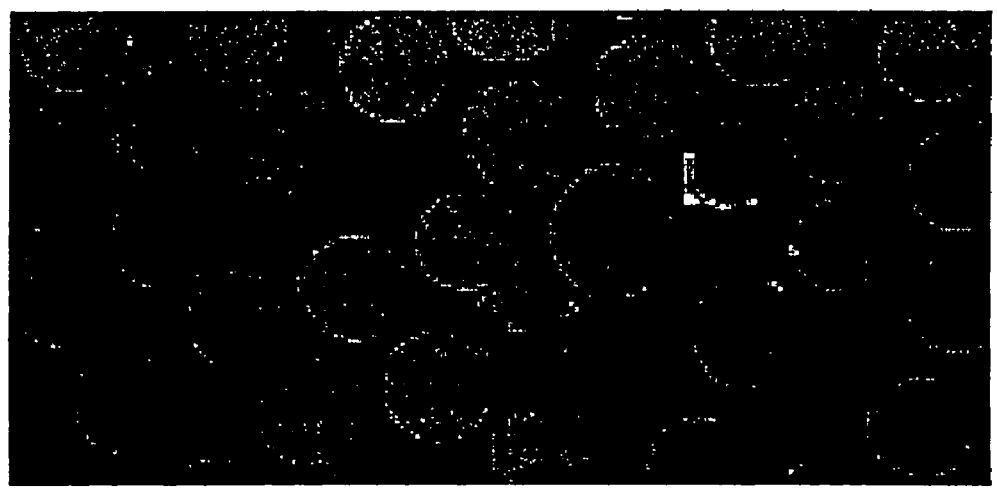

FIG. 7a shows theophylline-beads, mixed with antibodies mentioned in example 2. The high resolution shows that the locally raised concentration of fluorescent antibodies at the bead clearly differs from the background signal of the fluorescent antibodies being in solution. FIG. 7b shows the negative control without addition of the first antibody so that the second fluorescently marked antibody does not settle down at the bead and leads to the characteristic ring-structure in the picture.

In the following the invention is described in detail by the help of example 1 showing a specific embodiment of the method according to the invention as well as example 2 showing a concrete biological application.

EXAMPLE 1

The present example substantially corresponds to the arrangement shown in FIG. 6. A semiconductor laser 11 having a power of 3 mW and a wavelength of 780 nm is used as radiation source for generating the auxiliary focus 71. The output radiation of the laser 11 is directed to an optical fiber Y-coupling 42 by a monomode-glasfiber 81. Another monomode-glasfiber 80 at the exit of coupling 42 serves for supplying the radiation for the auxiliary focus 72 as well as for confocal detection of the light reflected at the interface 62.

An achromatic lens 31 having a focus of 40 mm serves for bundling the applied or detected radiation, respectively. The convergence of the ray bundles directed to the objective 32 and thereby the position of the auxiliary focus 71 relative to the measuring volume 70 can be variated by changing the distances between the free end of the fiber 80 and the achromatic lens 31 by lens mover portion 85. In the described embodiment the distance between measuring volume 70 and auxiliary focus 71 is adjustable from 0 to 100 µm by a displacement of the achromatic lens 31 by 5 mm.

The objective 32 used herein is a standard-microscope-objective having a 40-times magnification and a numerical aperture of 1.2. It is mounted on a piezoelectrical translator enabling a displacement of the objective over a distance of 100 µm from the optical axis. Conditional on the driving force of the translator as well as on the mass of the objectives used herein the limit frequency for this movement is about 400 Hz.

In this exemplary embodiment the transition from a glass support 61 (refraction index $n_1 \approx 1.52$) to the substrate 60, in this case consisting of an aqueous suspension of polymeric balls (refraction index $n_2 \approx 1.33$), is used as contact a surface 62. The radiation reflected from the interface 62 is directed over the objective 32 and the achromatic lens 31 once again on the fiber 80 the optical core of which taking over the function of the apertured diaphragm 51 shown in FIGS. 1 to 5, thus, ensuring a confocal detection. Over the coupling 42 50% of the radiation capacity reaches the detector 21 consisting of a cilium-photodiode with downstream transimpedanz amplifier (amplification $10^8$ v/a). The output signal of the detector 21 is supplied to a digital signal processor (DSP) by a 14-bit analog-digital-converter. Said DSP also controls the piezoelectrical translator of the objective 32 over a 14-bit digital-analog-converter and a downstream high voltage amplifier. For controlling the tracking the objective is moved upward and downward sinusoidally with a typical frequency of 200 Hz and an amplitude of 0,5 µm. Over demodulation of the intensity received by the detector 21, said demodulation being synchronous to said searching movement, the DSP determines the direction of a possible deviation between the position of the interface 62 and the position of the auxiliary focus 71 (taking the temporal mean over the sinusoidal movement). The determined deviation is compensated by a tracking of the objective 32, said tracking interfering the sinusoidal movement.

In the confocal measuring apparatus an active quenched Avalanche photodiode is used for as detector 20. The hole-diaphragm 50 has a diameter of 50 μm. A He—Ne-laser having an output wavelength of 543 nm, whose light capacity is reduced to 100 μW, serves as radiation source 10.

EXAMPLE 2

In the present example so called tenta-gel™—beads of the type S PHB-Gly (RAPP polymers) are used for the substrate. Those are conjugated with theophylline-molecules (Aldrich) as entities. The charging of the beads is 9%. 5 mg of the beads are suspended in 444 μl PBS-puffers. Lab-tek chambered coverglasses, #1 borosilicate, septic, 8-well (Nunc Nalge International, Lot. No. 148116-0605) are used as sample supports. A polyclonal rabbit anti-theopyllin-antibody (Europa Research, Lot. No. 80 17 15) is used as first antibody. A fluorescently marked (TRITC, Tetra-methylrhodamine-5-(and 6)-isothiocyanate) anti-rabbit-IgG-antibody (DAKO, Lot. No. 077(101)) serves as second antibody. The assay buffer, called TNT in the following, consists of: 50 mM Tris-HCl pH 7,5, 100 mM NaCl, 0,01% Tween-20.

The assay is done as follows: 8 μl bead suspension are mixed with 100 μl of a 1:2000 dilution of the first antibody and shaken for 30 minutes at room temperature. After that, the twice repeated washing step with TNT-buffer (0,01% Tween-20) is carried out. 100 μl of a dilution 1:5000 of the second antibody are added and shaken for one hour at room temperature. After that, 200 μl TNT-buffer are added.

A HeNe-laser with an emission wave length of 543 nm is used for generation of the trace of the rays of excitation with regard to the measuring volume 70. As a band filter suitable for the fluorescence-spectrum of TRITC a band pass on the side of detection is used having a mid-transition-wavelength of 580 nm and a half-intensity-width of 30 nm.

The result of example 2 is illustrated in FIGS. 7 *a* and *b*. The taken measuring values are first subjected to an image processing step serving for identification and localization of the single beads. To this the Hough-transformation is used in the described embodiment. Following, for each identified bead those measuring values are determined, which mark points on the bead-surface. To this, it is advantageously to use a-priori-information as in this case the expectation, that the optical cuts through the bead-surface lead to almost circular structures. In the present case, the measuring values of maximal intensity are determined along the searching paths extending radial from the center of the identified beads, respectively. Alternatively, the methods known from literature as edge-reinforcement and/or threshold-analysis may be used in this step.

The invention claimed is:

1. Method for optically detecting at least one entity chosen from the group consisting of molecules, molecule complexes, polymers, polymeric particles, particles built up from inorganic materials, vesicular structures, cells, bacteria and virus, comprising:
    arranging the at least one entity on and/or in a substrate, said substrate having a refraction-index which is different from the one of an at least one component adjacent to the substrate;
    scanning the at least one entity with a measuring volume using at least one device being confocal or configured for multi-photon-excitation, said device comprising a first radiation source and at least one first objective, thereby receiving measuring values of optical parameters which are processed by means of signal processing for characterization of the at least one entity;
    the at least one entity substantially maintains its position with respect to the substrate for the duration of receiving the measuring values,
    generating, before and/or during the scanning step, an auxiliary focus by means of at least one second radiation source and a second objective, said auxiliary focus is at least partly arranged on an interface between substrate and adjacent component or on another interface having a defined spacial relation to said entity;
    collimating the radiation generated by the first radiation source by a first optic and collimating the radiation generated by the second radiation source by a second optic being different from the first optic;
    detecting a retroreflection from the auxiliary focus by a detector having a confocal arranged diaphragm or by a plurality of detectors having diaphragms being arranged in front of and/or behind an image plane, and along the optical axis of the objective generating the auxiliary focus, said retroreflection is used for measuring position of the interface and, thus, for indirectly positioning the measuring volume; and
    adjusting position of the auxiliary focus relative to the measuring volume in a defined manner.

2. Method according to claim 1 wherein for indirectly positioning the measuring volume the auxiliary focus relative to the interface is moved both, laterally to the optical axis of the optic generating the auxiliary focus and axially.

3. Method according to claim 1 wherein the intensity of the retroreflection is detected by means of at least two detectors and the position of the interface is determined by means of the distribution of the intensities detected by the detectors.

4. Method according to claim 1 wherein the scatter-light-intensity and/or the scatter-light-intensity dependent on the polarization and/or the fluorescence-intensity at least one wavelength and/or the fluorescence-intensity in dependence on the polarization and/or the fluorescence-durability and/or molecular luminosity and/or Raman-scattering and/or luminescence are detected as optical parameters.

5. Method according to claim 1 wherein, in said step of arranging the at least one entity on and/or in a substrate, said substrate is a mineral or organic substrate chosen from the group consisting of a polymeric gel, a polymeric particle built up from inorganic material, a vesicular structure, a cell, a bacterium and a virus.

6. Method according to claim 1 wherein entities and/or substrates selected by means of the optical parameters are separated during or after the scanning process from the other entities and/or substrates.

7. The method according to claim 1, wherein said method for optically detecting further comprises a step of performing research of active ingredients, functional analysis of combinatoric-chemical or combinatoric-biological synthesis-products, functional genome-analysis, evolutive biotechnology, diagnostics, proteom-analysis, or the investigation of material.

8. Method according to claim 1, wherein said substrate is arranged on a support.

9. Method according to claim 1 wherein the extension of the confocal detected volume of the auxiliary focus in the direction of the optical axis of the first objective is smaller than the extension of the measuring volume in said direction.

10. Method according to claim 9 wherein the auxiliary focus for obtaining a smaller extension of the confocal detected volume of the auxiliary focus is generated by a second objective having a numeric aperture which is larger than the numeric aperture of the first objective used for generating the measuring volume.

11. Method according to claim 9 wherein for obtaining the small extension of the confocal detected volume of the auxiliary focus a smaller one of the numerical aperture of a common optic or the respective first optic and second optic is used for generating the measuring volume than for generating the auxiliary focus.

12. Method according to claim 9 wherein for obtaining a small extension of the confocal detected volume of the auxiliary focus, a confocal arranged diaphragm is used at the detection of the auxiliary focus, said diaphragm having a smaller opening than a confocal arranged diaphragm used at the detection of the measuring volume.

13. Method according to claim 1 wherein for indirectly positioning the measuring volume the auxiliary focus relative to the interface is moved substantially along the optical axis of the objective generating the auxiliary focus, the intensity of the retroreflection dependent on movement of the detector is registered and the position of the auxiliary focus is readjusted in a manner that the intensity of the retroreflection reaches its maximum.

14. Method according to claim 13 wherein the amplitude of the periodical movement of the auxiliary focus is smaller than or equal to the extension of the measuring volume in the direction of the optical axis of the first objective.

15. Method according to claim 13, wherein for indirectly positioning the measuring volume the auxiliary focus relative to the interface is moved periodically substantially along the optical axis of the objective generating the auxiliary focus.

16. Apparatus for performing the method according to claim 1 for optically detecting at least one entity chosen from the group consisting of molecules, molecule complexes, polymers, polymeric particles, particles built up from inorganic materials, vesicular structures, cells, bacteria or virus, comprising:
at least one first radiation source as well as at least one device being confocal or configured for multi-photon-excitation said device comprising a first objective and at least one first detector for detecting measuring values from the measuring volume;
at least a second radiation source as well as at least one further device comprising a second objective and at least one second detector for detecting a retroreflection from an auxiliary focus, said second detector having a confocal arranged diaphragm, or a plurality of second detectors for detecting a retroreflection from an auxiliary focus, said second detectors having diaphragms arranged in front of and/or behind an image plane, and along the optical axis of the second objective generating the auxiliary focus;
at least one device for positioning measuring volume and auxiliary focus relative to a substrate;
a device for variably positioning the auxiliary focus relative to the measuring volume;
a first optic collimating the radiation generated by the first radiation source; and
a second optic being different from the first optic collimating the radiation generated by the second radiation source.

17. Apparatus according to claim 16 wherein the device for positioning the measuring volume and the auxiliary focus relative to the substrate comprises means for positioning the auxiliary focus relative to the measuring volume.

18. Apparatus according to claim 16 wherein the device for positioning the auxiliary focus relative to the measuring volume comprises means for adjusting the relative position of the objectives to each other.

19. Apparatus according to claim 16 wherein the device for positioning the auxiliary focus relative to the measuring volume comprises means for variation of the convergence of bundles of rays that are focused by the respective objective for generation of the auxiliary focus and the measuring volume.

20. Method for optically detecting at least one entity chosen from the group consisting of molecules, molecule complexes, polymers, polymeric particles, particles built up from inorganic materials, vesicular structures, cells, bacteria and virus, comprising:
arranging the at least one entity on and/or in a substrate, said substrate having a refraction-index which is different from the one of an at least one component adjacent to the substrate,
scanning the at least one entity with a measuring volume using at least one device being confocal or configured for multi-photon-excitation, said device comprising a first radiation source and at least one objective, thereby receiving measuring values of optical parameters which are processed by means of signal processing for characterization of the at least one entity,
the at least one entity substantially maintains its position with respect to the substrate for the duration of the scanning,
generating, before and/or during the scanning step, an auxiliary focus by means of at least one second radiation source and the objective, said auxiliary focus is at least partly arranged on an interface between substrate and adjacent component or on another interface having a defined spacial relation to said entity,
collimating the radiation generated by the first radiation source by a first optic and collimating the radiation generated by the second radiation source by a second optic being different from the first optic,
detecting a retroreflection from the auxiliary focus by a detector having a confocal arranged diaphragm or by a plurality of detectors having diaphragms being arranged in front of and/or behind an image plane, and along the optical axis of the objective generating the auxiliary focus, said retroreflection for measuring position of the interface and, thus, for indirectly positioning the measuring volume, and
adjusting position of the auxiliary focus relative to the measuring volume in a defined manner,
wherein for indirectly positioning the measuring volume, the auxiliary focus relative to the interface is moved substantially along the optical axis of the objective generating the auxiliary focus, the intensity of the retroreflection dependent on movement of the detector is registered and the position of the auxiliary focus is readjusted in a manner that the intensity of the retroreflection reaches its maximum.

21. Method according to claim 20, wherein said substrate is arranged on a support.

22. Method according to claim 20 wherein the extension of the confocal detected volume of the auxiliary focus in the direction of the optical axis of the objective is smaller than the extension of the measuring volume in said direction.

23. Method according to claim 22 wherein for obtaining the small extension of the confocal detected volume of the auxiliary focus a smaller one of the numerical aperture of a common optic or the respective first optic and second optic is used for generating the measuring volume than for generating the auxiliary focus.

24. Method according to claim 20 wherein the amplitude of the periodical movement of the auxiliary focus is smaller than or equal to the extension of the measuring volume in the direction of the optical axis of the objective.

25. Method according to claim 20 wherein the scatter-light-intensity and/or the scatter-light-intensity dependent on the polarization and/or the fluorescence-intensity at least one wavelength and/or the fluorescence-intensity in dependence on the polarization and/or the fluorescence-durability and/or molecular luminosity and/or Raman-scattering and/or luminescence are detected as optical parameters.

26. The method according to claim 20, wherein said method for optically detecting further comprises a step of performing research of active ingredients, functional analysis of combinatoric-chemical or combinatoric-biological synthesis-products, functional genome-analysis, evolutive biotechnology, diagnostics, proteom-analysis, or the investigation of material.

27. Method according to claim 20, wherein for indirectly positioning the measuring volume the auxiliary focus relative to the interface is moved periodically substantially along the optical axis of the objective generating the auxiliary focus.

28. Apparatus for performing a method for optically detecting at least one entity chosen from the group consisting of molecules, molecule complexes, polymers, polymeric particles, particles built up from inorganic materials, vesicular structures, cells, bacteria and virus, comprising:
    arranging the at least one entity on and/or in a substrate, said substrate having a refraction-index which is different from the one of an at least one component adjacent to the substrate,
    scanning the at least one entity with a measuring volume using at least one device being confocal or configured for multi-photon-excitation, said device comprising a first radiation source and at least one objective, thereby receiving measuring values of optical parameters which are processed by means of signal processing for characterization of the at least one entity,
    the at least one entity substantially maintains its position with respect to the substrate for the duration of the scanning,
    generating, before and/or during the scanning step, an auxiliary focus by means of at least one second radiation source and the objective, said auxiliary focus is at least partly arranged on an interface between substrate and adjacent component or on another interface having a defined spacial relation to said entity,
    collimating the radiation generated by the first radiation source by a first optic and collimating the radiation generated by the second radiation source by a second optic being different from the first optic,
    detecting a retroreflection from the auxiliary focus by a detector having a confocal arranged diaphragm or by a plurality of detectors having diaphragms being arranged in front of and/or behind an image plane, and along the optical axis of the objective generating the auxiliary focus, said retroreflection for measuring position of the interface and, thus, for indirectly positioning the measuring volume, and
    adjusting position of the auxiliary focus relative to the measuring volume in a defined manner, said method optically detecting at least one entity chosen from the group consisting of molecules, molecule complexes, polymers, polymeric particles, particles built up from inorganic material, vesicular structures, cells, bacteria or virus, the apparatus having
    at least one first radiation source as well as at least one device being confocal or configured for multi-photon-excitation said device comprising an objective and at least one first detector for detecting measuring values from a measuring volume,
    at least one second radiation source as well as at least one further device comprising the same objective and a second detector for detecting a retroreflection from an auxiliary focus, the second detector having a confocal arranged diaphragm, or a plurality of second detectors for detecting a retroreflection from an auxiliary focus, said second detectors having diaphragms arranged in front of and/or behind the image plane and along the optical axis of the objective generating the auxiliary focus,
    at least one device for positioning the measuring volume and auxiliary focus relative to the substrate,
    a device for relative positioning the auxiliary focus relative to the measuring volume,
    a first optic collimating the radiation generated by the first radiation source, and
    a second optic different from the first optic collimating the radiation generated by the second radiation source,
    wherein the device for positioning the auxiliary focus relative to the measuring volume comprises means for variation of the convergence of bundles of rays that are focused by the respective objective for generation of the auxiliary focus and the measuring volume.

29. Apparatus according to claim 28 wherein the device for positioning the measuring volume and the auxiliary focus relative to the substrate comprises means for positioning the auxiliary focus relative to the measuring volume.

30. Method for optically detecting at least one entity chosen from the group consisting of molecules, molecule complexes, polymers, polymeric particles, particles built up from inorganic materials, vesicular structures, cells, bacteria and virus, comprising:
    arranging the at least one entity on and/or in a substrate, said substrate having a refraction-index which is different from the one of an at least one component adjacent to the substrate,
    scanning the at least one entity with a measuring volume using at least one device being confocal or configured for multi-photon-excitation, said device comprising a first radiation source and at least one objective, thereby receiving measuring values of optical parameters which are processed by means of signal processing for characterization of the at least one entity,
    the at least one entity substantially maintains its position with respect to the substrate for the duration of the scanning,
    generating, before and/or during the scanning step, an auxiliary focus by means of at least one second radiation source and the objective, said auxiliary focus is at least partly arranged on an interface between substrate and adjacent component or on another interface having a defined spacial relation to said entity,
    collimating the radiation generated by the first radiation source by a first optic and collimating the radiation generated by the second radiation source by a second optic being different from the first optic,
    detecting a retroreflection from the auxiliary focus by a detector having a confocal arranged diaphragm or by a plurality of detectors having diaphragms being arranged in front of and/or behind an image plane, and along the optical axis of the objective generating the auxiliary focus, said retroreflection for measuring position of the interface and, thus, for indirectly positioning the measuring volume, and adjusting position of the auxiliary focus relative to the measuring volume in a defined manner, wherein the extension of the confocal detected volume of the auxiliary focus in the direction of the optical axis of the objective is smaller than the extension of the measuring volume in said direction, wherein for obtaining the small extension of the confocal detected volume of the auxiliary focus a confocal arranged diaphragm is used at the detection of the auxiliary focus, said diaphragm having a smaller opening than a confocal arranged diaphragm used at the detection of the measuring volume.

31. Method for optically detecting at least one entity chosen from the group consisting of molecules, molecule complexes, polymers, polymeric particles, particles built up from inorganic materials, vesicular structures, cells, bacteria and virus, comprising:

arranging the at least one entity on and/or in a substrate, said substrate having a refraction-index which is different from the one of an at least one component adjacent to the substrate, scanning the at least one entity with a measuring volume using at least one device being confocal or configured for multi-photon-excitation, said device comprising a first radiation source and at least one objective, thereby receiving measuring values of optical parameters which are processed by means of signal processing for characterization of the at least one entity, the at least one entity substantially maintains its position with respect to the substrate for the duration of the scanning, generating, before and/or during the scanning step, an auxiliary focus by means of at least one second radiation source and the objective, said auxiliary focus is at least partly arranged on an interface between substrate and adjacent component or on another interface having a defined spacial relation to said entity, collimating the radiation generated by the first radiation source by a first optic and collimating the radiation generated by the second radiation source by a second optic being different from the first optic, detecting a retroreflection from the auxiliary focus by a detector having a confocal arranged diaphragm or by a plurality of detectors having diaphragms being arranged in front of and/or behind an image plane, and along the optical axis of the objective generating the auxiliary focus, said retroreflection for measuring position of the interface and, thus, for indirectly positioning the measuring volume, and adjusting position of the auxiliary focus relative to the measuring volume in a defined manner, wherein for indirectly positioning the measuring volume the auxiliary focus relative to the interface is moved both, laterally to the optical axis of the optic generating the auxiliary focus and axially.

32. Method for optically detecting at least one entity chosen from the group consisting of molecules, molecule complexes, polymers, polymeric particles, particles built up from inorganic materials, vesicular structures, cells, bacteria and virus, comprising:

arranging the at least one entity on and/or in a substrate, said substrate having a refraction-index which is different from the one of an at least one component adjacent to the substrate, scanning the at least one entity with a measuring volume using at least one device being confocal or configured for multi-photon-excitation, said device comprising a first radiation source and at least one objective, thereby receiving measuring values of optical parameters which are processed by means of signal processing for characterization of the at least one entity, the at least one entity substantially maintains its position with respect to the substrate for the duration of the scanning, generating, before and/or during the scanning step, an auxiliary focus by means of at least one second radiation source and the objective, said auxiliary focus is at least partly arranged on an interface between substrate and adjacent component or on another interface having a defined spacial relation to said entity, collimating the radiation generated by the first radiation source by a first optic and collimating the radiation generated by the second radiation source by a second optic being different from the first optic, detecting a retroreflection from the auxiliary focus by a detector having a confocal arranged diaphragm or by a plurality of detectors having diaphragms being arranged in front of and/or behind an image plane, and along the optical axis of the objective generating the auxiliary focus, said retroreflection for measuring position of the interface and, thus, for indirectly positioning the measuring volume, and adjusting position of the auxiliary focus relative to the measuring volume in a defined manner, wherein the intensity of the retroreflection is detected by means of at least two detectors and the position of the interface is determined by means of the distribution of the intensities detected by the detectors.

33. Method for optically detecting at least one entity chosen from the group consisting of molecules, molecule complexes, polymers, polymeric particles, particles built up from inorganic materials, vesicular structures, cells, bacteria and virus, comprising:

arranging the at least one entity on and/or in a substrate, said substrate having a refraction-index which is different from the one of an at least one component adjacent to the substrate, scanning the at least one entity with a measuring volume using at least one device being confocal or configured for multi-photon-excitation, said device comprising a first radiation source and at least one objective, thereby receiving measuring values of optical parameters which are processed by means of signal processing for characterization of the at least one entity, the at least one entity substantially maintains its position with respect to the substrate for the duration of the scanning, generating, before and/or during the scanning step, an auxiliary focus by means of at least one second radiation source and the objective, said auxiliary focus is at least partly arranged on an interface between substrate and adjacent component or on another interface having a defined spacial relation to said entity, collimating the radiation generated by the first radiation source by a first optic and collimating the radiation generated by the second radiation source by a second optic being different from the first optic, detecting a retroreflection from the auxiliary focus by a detector having a confocal arranged diaphragm or by a plurality of detectors having diaphragms being arranged in front of and/or behind an image plane, and along the optical axis of the objective generating the auxiliary focus, said retroreflection for measuring position of the interface and, thus, for indirectly positioning the measuring volume, and adjusting position of the auxiliary focus relative to the measuring volume in a defined manner, wherein, in said step of arranging the at least one entity on and/or in a substrate, said substrate is a mineral or organic substrate chosen from the group consisting of a polymeric gel, a polymeric particle built up from inorganic material, a vesicular structure, a cell, a bacterium and a virus.

34. Method for optically detecting at least one entity chosen from the group consisting of molecules, molecule complexes, polymers, polymeric particles, particles built up from inorganic materials, vesicular structures, cells, bacteria and virus, comprising:

arranging the at least one entity on and/or in a substrate, said substrate having a refraction-index which is different from the one of an at least one component adjacent to the substrate, scanning the at least one entity with a measuring volume using at least one device being confocal or configured for multi-photon-excitation, said device comprising a first radiation source and at least one objective, thereby receiving measuring values of optical parameters which are processed by means of signal processing for characterization of the at least one entity, the at least one entity substantially maintains its position with respect to the substrate for the duration of the scanning, generating, before and/or during the scanning step, an auxiliary focus by means of at least one second radiation source and the objective, said auxiliary focus is at least partly arranged on an interface between substrate and adjacent component or on another interface having a defined spacial relation to said entity, collimating the radiation generated by the first radiation source by a first optic and collimating the radiation generated by the second radiation source by a second optic being different from the first optic, detecting a retroreflection from the auxiliary focus by a detector having a confocal arranged diaphragm or by a plurality of detectors having diaphragms being arranged in front of and/or behind an image plane, and along the optical axis of the objective generating the auxiliary focus, said retroreflection for measuring position of the interface and, thus, for indirectly positioning the measuring volume, and adjusting position of the auxiliary focus relative to the measuring volume in a defined manner, wherein entities and/or substrates selected by means of the optical parameters are separated during or after the scanning process from the other entities and/or substrates.

* * * * *

UNITED STATES PATENT AND TRADEMARK OFFICE
CERTIFICATE OF CORRECTION

| | |
|---|---|
| PATENT NO. | : 7,202,953 B1 |
| APPLICATION NO. | : 09/868845 |
| DATED | : April 10, 2007 |
| INVENTOR(S) | : Juergen Mueller et al. |

It is certified that error appears in the above-identified patent and that said Letters Patent is hereby corrected as shown below:

On the Title Page, Item (30)

Domestic Priority Data, should read:

--Dec. 21, 1998    60/113,478--

On the Title Page, Item (22)

"Dec. 21, 1999" should read --Dec. 20, 1999--

Signed and Sealed this

Twenty-first Day of August, 2007

JON W. DUDAS
*Director of the United States Patent and Trademark Office*